June 4, 1929. F. E. PARKLER Re. 17,319

VAGINAL SYRINGE

Original Filed Feb. 21, 1924

Inventor:
Fritz E. Parkler.
By Mason Fenwick & Lawrence
Attys

Reissued June 4, 1929. Re. 17,319

UNITED STATES PATENT OFFICE.

FITZ E. PARKLER, OF CHICAGO HEIGHTS, ILLINOIS.

VAGINAL SYRINGE.

Original No. 1,583,487, dated May 4, 1926, Serial No. 694,397, filed February 21, 1924. Application for reissue filed September 22, 1926 Serial No. 137,141.

This invention relates to an improvement in syringes, and more particularly, to a vaginal syringe which will be used to thoroughly cleanse the walls of the vagina.

The object of the invention is to provide a suitable construction of syringe which will be formed with a plurality of discharge openings through which a cleansing fluid may be sprayed, to thoroughly cleanse and irrigate the walls of the vagina, and an integrally formed outlet or drain groove whereby the liquid may be removed or drained from the vagina after the same has been cleansed without removal from the body.

The further object of the invention is to provide a vaginal syringe which will be provided with means for discharging a cleansing fluid therethrough, together with means for draining the liquid from the interior of the vagina, and means for regulating the flow of the liquid to and from the syringe, as desired.

Other objects will appear as the description proceeds.

In the accompanying drawings which form a part of my application,

Like characters of reference are used throughout the following specification and the accompanying drawings to designate corresponding parts.

Figure 1:
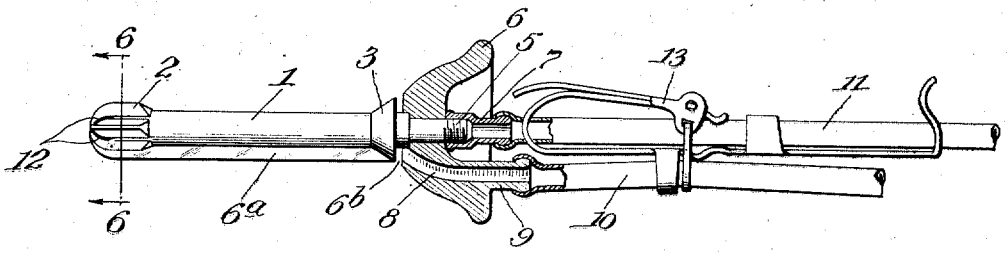
Figure 1 is a side elevation partly in section showing my improvement in vaginal springes.
Figure 2:
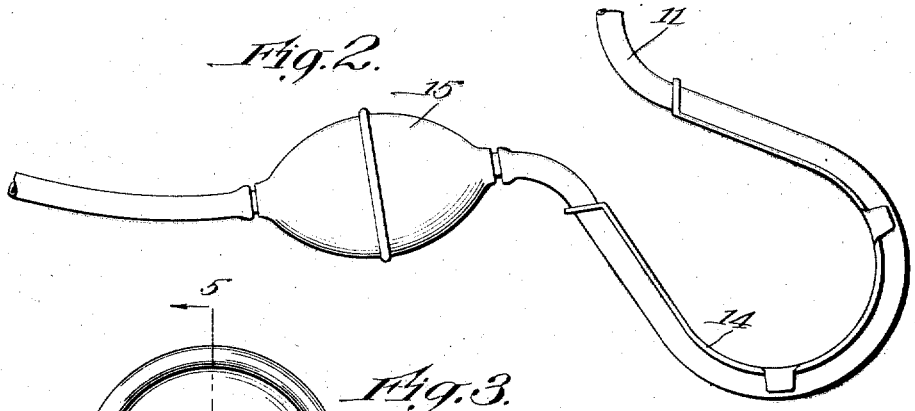
Figure 2 is a side elevation of the fluid supply tube and the valved pressure bulb.
Figure 3:
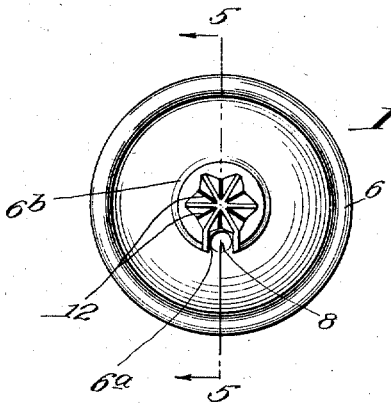
Figure 3 is a front elevation of my improvement.
Figure 4:
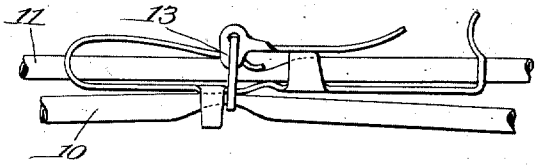
Figure 4 is a side elevation of the regulating means for the fluid.
Figure 5:
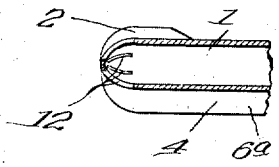
Figure 5 is a longitudinal sectional view taken on the line 5—5 of the Figure 3.
Figure 6:
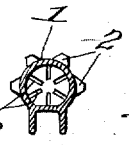
Figure 6 is a transverse sectional view taken on the line 6—6 of the Figure 1.

My invention comprises an elongated injection tube 1, which is provided at its forward or nozzle end with a plurality of radially extending flanges 2, which extend around to the tip of the nozzle and are tapered at said end and give a star shaped appearance to the forward end of the said tube. An annular inwardly and forwardly tapered flange or collar 3 is formed adjacent the rear end of the tube 1 and is connected with the downwardly facing outlet or drain groove 4 along the bottom, which extends the full length of said tube. This groove is formed by a pair of depending parallel flanges 6[a] providing a relatively deep groove to prevent the wall of the vagina from projecting into the groove and closing the same, but permitting the tissues to seal the open side of the groove against the edges of the flanges to provide an unobstructed drain therethrough.

The injection tube is threaded at its inner end as at 5, and is adapted to support the stopper or shield 6, the inner end of which is spaced a slight distance from the adjacent large end of the collar 3, thereby forming an air gap or annular part 6[b]. A hollow nipple 7 is threaded on to the inner end of the tube 1 and serves to hold the stopper 6 in place. The stopper 6 is provided with an outlet or drain passage 8 which is in aline with the open end of the drain groove 4 and terminates with the extension 9, which is adapted to receive the flexible drain tube 10. The stopper 6 seals the mouth of the vagina until the supply of cleansing fluid is exhausted whereupon the tissues around the mouth of the vagina close.

A supply pipe or tube 11 is adapted to be secured to the outer end of the nipple 7, and to conduct the cleansing fluid from a supply receptacle (not shown).

The injection tube 1 is provided at its forward end with a plurality of narrow discharge slots 12, which are positioned between the several radially extending flanges to discharge the fluid in thin sprays or sheets at all sides, thereby insuring thorough cleansing.

The regulating clamp 13 is adapted to be positioned over the tubes 10 and 11 in such a manner that both tubes may be compressed to stop the flow of liquid through the same, or the drain tube may be partially closed prior to the closing of the inlet or supply tube, for purposes hereinafter described. When the clamp 13 is in the position as illustrated in Figure 1 of the drawings, both tubes will be open to freely pass the fluid.

A suitable spring member 14 will be positioned above the supply tube 11 to prevent same from being kinked, and a valved bulb 15 will also be inserted in the supply line so that by squeezing the same pressure may be applied to the fluid as it is discharged from the discharge slots 12 at the outer end of the injection tube.

The operation of the vaginal syringe will now be described: The person desiring to use the syringe lies flat on the back, and the injection tube will be inserted into the mouth of the vagina until the stopper 6 completely seals the same and the part $6^b$ is spanned to establish a passage across said part between groove 4 and passage 8. The inner end of the injection tube will then be directly in front of the mouth of the womb, so that with the clamp 13 open, the cleansing fluid may freely pass therethrough and be discharged from the slots 12, at the bottom of the vagina from where it is forced upward the entire length of vagina; this action causes the mouth of the vagina to open sufficiently to allow the cleansing fluid to drain into the gap $6^b$ and through drain passage 8 and drain tube 10 into a receptacle on the floor. The said process continues until the supply of fluid is exhausted, thereby thoroughly cleansing and irrigating the walls of the vagina and the entrance to the womb and thereafter the vagina again seals the gap $6^b$. When it is desired to dilate the walls of the vagina, the clamp 13 will be slightly closed to partially close the drain tube 10 which will permit a faster flow of liquid into the interior of the vagina than the outflow of the fluid therefrom. This will cause the fluid to collect within the vagina and consequently dilate the walls thereof so that all of the fold may be thoroughly irrigated.

When the supply of cleansing fluid has been exhausted, there will be a difference of height in the fluid in the drain tube and the supply tube and in view of the pressure of air in the supply tube, there will be a siphoning action which will drain all of the liquid from the interior of the vagina. In most syringes it is practically impossible to use the same while the person is on their back, but with my device it will be quite simple to thoroughly and efficiently manipulate the syringe so that the interior walls of the vagina will be thoroughly cleansed and irrigated, and the fluid which would remain therein, due to the fact that the mouth of the vagina is on a higher level than the interior thereof, will be positively siphoned therefrom.

If it is desired to secure a greater pressure of the fluid than is possible by having the source of supply elevated above the injection tube, it is made possible by using the valved bulb 15.

It will be understood that while I have described my preferred form of vaginal syringe, I do not intend to limit myself to the specified construction of same, as many minor changes in detail of construction may be resorted to without departure from the spirit of the invention.

Having thus described my invention, what I claim is:

1. In a syringe, a hollow injection tube, a shield mounted upon the said tube, and held in place at one end by a raised shoulder, and at the front by a threaded nipple, the threaded nipple attached to the end of the said tube, and resting against the concave face of the said shield, the said nipple having at its outer end means for attaching a rubber tube and holding the said tube thereon.

2. A vaginal syringe, a hollow injection tube having a plurality of radially extending flanges at the nozzle only, said nozzle having a plurality of narrow discharge slots formed between said flanges to discharge the fluid in spray sheets, the bottom of the syringe having a grooved drain projecting therefrom at its periphery and of uniform width throughout its depth on the exterior of the injection tube and throughout the length thereof, an outwardly flared collar at the opposite ends of the tube, inner end of the grooved drain terminating adjacent said collar and having a discharge opening therethrough, a shield mounted upon said tube in rear of the collar and spaced therefrom, means connected to said tube for supplying a cleansing fluid thereto, said shield having an outlet passage for draining the vagina from said drain and terminating in line with said drain, and a drain pipe connected to said outlet, the mouth of the vagina being adapted to fit around the outer portion of the drain groove so as to span the drain groove without closing the same and across the collar and shield to effect a continuation of the groove through the shield to the outlet.

3. A vaginal syringe, a hollow injection tube having a plurality of radially extending flanges formed at the outer end thereof, a plurality of discharge slots being formed between said flanges, a pair of substantially parallel flanges extending from the bottom of the tube throughout its length and forming a drain groove along the same of a depth at least as great as its width, an anular flange on the tube at the rear end of the groove, a shield secured on tube in rear of the collar and having a drain opening therethrough curved toward the collar with a space between the two adapted to be closed over by the walls of the vagina without closing said space to form a continuation of the drain groove, and the open side of said groove being closed by the walls of the vagina across the edges of the flanges with the front end open and without obstructing said groove, a tube connected to the injection tube for supplying the cleansing fluid thereto, and a tube connected to the drain for draining the vagina.

4. A syringe comprising a hollow injection tube, there being narrow radial discharge slots at the outer end thereof, a drain groove formed on the outer surface of said tube comprising a pair of spaced walls, extending the whole length of said tube, and disposed in angular relation less than an obtuse angle so that the groove is of no greater width than its depth at any point on its length, a stopper positioned at the inner end of said tube in spaced relation with said drain groove, said stopper being provided with a discharge passage, separate means for conducting the cleansing fluid to and from said tube, means for regulating the flow of said fluid, and means for selectively opening or closing said fluid conducting means.

5. A syringe comprising a hollow injection tube, a plurality of radially extending flanges formed at the outer end thereof, discharge slots being positioned between said flanges, flanges extending from the periphery of the tube throughout the length thereof at the bottom and forming a drain groove throughout the length of the tube of uniform width and depth throughout its length, said groove being approximately as deep as it is wide, and means to conduct and drain a cleansing fluid to and from the nozzle and drain groove respectively.

6. A syringe comprising a hollow injection tube, a plurality of radially extending flanges formed at the outer end thereof, discharge slots being positioned between said flanges, flanges extending from the periphery of the tube throughout the length thereof at the bottom and forming a drain groove throughout the length of the tube, open at both ends in alignment with the groove, said groove being approximately as deep as it is wide, a stopper positioned at the inner end of said tube in spaced relation with said drain groove, said stopper being provided with an outlet passage in alignment with said drain groove, means for conducting a cleansing fluid through said tube, means for conducting said fluid from said outlet passage, and means for selectively opening or closing said fluid conducting means and for simultaneously closing the same whereby to supply the fluid without discharge for dilating the vagina or for creating a siphoning action to discharge all of the cleansing fluid from the vagina through said groove and portions of the vagina positioned therebeneath.

7. A vaginal syringe comprising a hollow injection tube, discharge slots at the outer end thereof, grooved channel formed along the bottom of the tube from tip to rear end thereof open at both ends and having spaced substantially parallel walls forming a relatively deep groove of a depth at least as great as its width, a collar on the rear end of the tube, a stopper positioned at the inner end of said tube in spaced relation to the collar and drain groove and provided with a discharge passage in line with and forming a continuation of the drain groove, said stopper being adapted to fit the vagina whereby the latter will seal the space between the collar and the stopper and also the open side of the tube, separate means for conducting the cleansing fluid to and from said tube, means for regulating the flow of said fluid, said means by a single operation serving to individually open or close said conducting means or to simultaneously close the same, and adapted to affect the siphoning action in the grove when a supply of cleansing fluid has been exhausted from the conducting means whereby to entirely drain the bottom of the vagina.

8. In a vaginal syringe, a round hollow injection tube having a pair of spaced parallel walls projecting from the bottom thereof in the direction of chords of an arc of the circle of the tube forming a drain groove of uniform width and substantially as deep as it is wide, and a plurality of radially extended forwardly tapered flanges at extreme forward end of the tube upon the exterior surface thereof and terminating at the extreme forward end of the tube, there being slots between said flanges.

9. A syringe of the class described, including a round hollow injection tube having a pair of spaced parallel flanges along the bottom thereof parallel to the axis of the tube and with their outer edges in the same horizontal plane, forming a drain groove extending from the tip end of the injection tube to the rear end thereof and being of uniform width throughout its depth and length, the depth being at least as great as its width and said drain groove being open at both ends, radial flanges on the periphery of the tube extending from near the forward end of the tube to the tip thereof, the tip end of the tube wall having radial slots therein between the flanges, means for conveying fluid through the tube, and means leading from the rear end of the groove to drain the same.

10. In a vaginal syringe, a nozzle having discharge slots in its tip and a bottom groove externally throughout its length, a shield on the inner end of the tube and having a drain extension leading to the rear of the groove, an axial supply tube connected with the nozzle in rear of the shield, a drain tube connected to the extension, fluid supply means connected to the supply tube, and a regulating clamp on the tubes, said clamp having engagement with both tubes and provided with means to simultaneously close the same, to partially close the drain tube prior to closing the supply tube or to leave both tubes freely open.

11. A syringe of the class described comprising a hollow injection tube, there being a discharge hole at the outer end thereof, a drain groove formed on the outer surface of said tube comprising a pair of spaced walls extending the whole length of the tube and disposed in angular relation less than an obtuse angle so that the groove is of no greater width than its depth at any point on its length, means for conducting cleansing fluid to said tube and a drain leading from the inner end of the drain groove.

FITZ EDWARD PARKLER.